(12) United States Patent
Deur-Bert et al.

(10) Patent No.: US 11,459,286 B2
(45) Date of Patent: Oct. 4, 2022

(54) METHOD FOR MODIFYING FLUORINE DISTRIBUTION IN A HYDROCARBON COMPOUND

(71) Applicant: Arkema France, Colombes (FR)

(72) Inventors: Dominique Deur-Bert, Charly (FR); Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 34 days.

(21) Appl. No.: 16/618,866

(22) PCT Filed: Jun. 5, 2018

(86) PCT No.: PCT/EP2018/064713
§ 371 (c)(1),
(2) Date: Dec. 3, 2019

(87) PCT Pub. No.: WO2018/224476
PCT Pub. Date: Dec. 13, 2018

(65) Prior Publication Data
US 2021/0114955 A1  Apr. 22, 2021

(30) Foreign Application Priority Data
Jun. 6, 2017 (FR) ..................................... 1754981

(51) Int. Cl.
| | |
|---|---|
| *C07C 17/358* | (2006.01) |
| *C07C 17/093* | (2006.01) |
| *C07C 17/10* | (2006.01) |
| *C07C 17/12* | (2006.01) |
| *C07C 17/14* | (2006.01) |
| *C07C 17/20* | (2006.01) |
| *C07C 17/37* | (2006.01) |
| *C07C 17/21* | (2006.01) |
| *C07C 17/25* | (2006.01) |
| *C07C 17/367* | (2006.01) |
| *B01J 19/02* | (2006.01) |
| *B01J 23/26* | (2006.01) |
| *C07C 19/08* | (2006.01) |
| *C07C 19/10* | (2006.01) |
| *C07C 21/18* | (2006.01) |

(52) U.S. Cl.
CPC ............ *C07C 17/358* (2013.01); *B01J 19/02* (2013.01); *B01J 23/26* (2013.01); *C07C 17/093* (2013.01); *C07C 17/10* (2013.01); *C07C 17/12* (2013.01); *C07C 17/14* (2013.01); *C07C 17/20* (2013.01); *C07C 17/206* (2013.01); *C07C 17/21* (2013.01); *C07C 17/25* (2013.01); *C07C 17/367* (2013.01); *C07C 17/37* (2013.01); *C07C 19/08* (2013.01); *B01J 2219/0236* (2013.01); *B01J 2219/0286* (2013.01); *C07C 19/10* (2013.01); *C07C 21/18* (2013.01)

(58) Field of Classification Search
CPC ..................................................... C07C 17/206
See application file for complete search history.

(56) References Cited

U.S. PATENT DOCUMENTS

| | | | | |
|---|---|---|---|---|
| 5,565,393 | A | * | 10/1996 | Felix ........................ B01J 19/02 422/241 |
| 2003/0060669 | A1 | * | 3/2003 | Shibata .................. C07C 17/206 570/136 |
| 2005/0019487 | A1 | | 1/2005 | Braun et al. |
| 2005/0020862 | A1 | * | 1/2005 | Tung ....................... C07C 17/25 570/164 |
| 2009/0240090 | A1 | | 9/2009 | Merkel et al. |
| 2011/0015452 | A1 | | 1/2011 | Devic et al. |
| 2014/0066670 | A1 | | 3/2014 | Cottrell |
| 2016/0145175 | A1 | * | 5/2016 | Deur-Bert .............. B01J 23/866 570/160 |
| 2017/0021319 | A1 | * | 1/2017 | Dassel ....................... B01J 8/18 |

FOREIGN PATENT DOCUMENTS

| | | |
|---|---|---|
| WO | 9406554 A1 | 3/1994 |
| WO | 2009118630 A1 | 10/2009 |

OTHER PUBLICATIONS

McHoneIndustries "A Guide to Carbon Steel Grades (Plus a Chart)" Jun. 3, 2020; pp. 1-5 (Year: 2020).*
MAT21 (SNSMT "Hex Socket Head Cap Screws (MAT21)", p. 1) (Year: 2022).*
Steel ("General Properties of Steels", p. 1) (Year: 2021).*
ISA/EP; International Search Report and Written Opinion for International Patent Application No. PCT/EP2018/064713 dated Jun. 20, 2018.
"New Edition of Steel Technology Lectures: 4. Steel Processing", Japan Iron and Steel Association, Shanghai Science and Technology Press, vol. 4, May 1982, 8 pages.
Liu, Jiwen, et al.,"Introduction to Petrochemical Equipment and Manufacturing", Harbin Institute of Ship Engineering Press, Jul. 1989, 8 pages.

* cited by examiner

*Primary Examiner* — Medhanit W Bahta
(74) *Attorney, Agent, or Firm* — NK Patent Law

(57) ABSTRACT

The present invention relates to a process for modifying the fluorine distribution in a hydrocarbon compound, comprising a step of making contact between said hydrocarbon compound and a catalytic composition comprising a chromium-based catalyst, said process being performed in a reactor made of a material comprising a base layer made of a material M1 and an inner layer made of a material M2, said base layer and said inner layer being laid against each other by bonding.

14 Claims, No Drawings

METHOD FOR MODIFYING FLUORINE DISTRIBUTION IN A HYDROCARBON COMPOUND

CROSS-REFERENCE TO RELATED APPLICATIONS

This application is a U.S. National Stage application of International Patent Application No. PCT/EP2018/064713, filed on Jun. 5, 2018, which claims the benefit of French Patent Application No. 1754981, filed on Jun. 6, 2017.

TECHNICAL FIELD

The present invention relates to processes for modifying the distribution of fluorine in the gas phase. In particular, the present invention relates to processes for modifying the distribution of fluorine in the gas phase in the presence of a chromium-based catalyst.

TECHNOLOGICAL BACKGROUND OF THE INVENTION

Halogenated hydrocarbons, in particular fluorinated hydrocarbons, such as hydrofluoroolefins, are compounds which have a structure of use as functional materials, solvents, refrigerants, inflating agents and monomers for functional polymers or starting materials for such monomers. Hydrofluoroolefins, such as 2,3,3,3-tetrafluoropropene (HFO-1234yf), are attracting attention because they offer a promising behavior as refrigerants having a low global warming potential.

Processes for the production of fluoroolefins are usually carried out in the presence of a starting substance, such as a chlorine-containing alkane or a chlorine-containing alkene, and in the presence of a fluorinating agent, such as hydrogen fluoride. These processes can be carried out in the gas phase or in the liquid phase, in the absence or not of a catalyst.

The gas-phase processes are usually performed in the presence of catalysts and of hydrofluoric acid. The environment inside the catalytic reactor exhibits very high acidity, giving rise to high corrosion of the material of the reactor. The reactors used in processes involving hydrofluoric acid generally comprise a base material and a corrosion-resistant material. The base material and the corrosion-resistant material may be assembled via various techniques in which the materials are or are not melted. Depending on the assembly technique used, the properties of the materials may be different.

For example, when the materials are melted, weaknesses may appear at the interface thereof over time in the presence of an acidic environment.

The assembly of materials by bonding (without melting of the materials) is an inexpensive technique. However, U.S. Pat. No. 5,565,393 discloses a fluorination process performed in a reactor, the materials of which are assembled by bonding in the presence of a catalyst of tantalum, niobium or antimony type. The materials which corrode the least are alloys of molybdenum/rhenium or tungsten/rhenium type or gold-based alloys. The cost of this type of alloy is too high to be applicable on an industrial scale. In addition, the rate of corrosion of the materials used is greater than 10 mm/year. The rate of corrosion is also much too high to allow the use of a reactor prepared via this technique. Reactors whose materials are assembled by bonding are therefore incompatible with fluorination processes under the conditions described by U.S. Pat. No. 5,565,393.

There is thus a need for fluorination processes performed under conditions which minimize corrosion and increase the lifetime of a catalyst.

SUMMARY OF THE INVENTION

The Applicant has found, surprisingly, that in the presence of a chromium-based catalyst, the corrosion of the materials used in a fluorination reactor when these materials are assembled by bonding is greatly reduced, allowing the use of a reliable process that is economically viable on an industrial scale.

According to a first aspect, the invention provides a process for modifying the fluorine distribution in a hydrocarbon compound, comprising a step of making contact between said hydrocarbon compound and a catalytic composition comprising a chromium-based catalyst, said process being performed in a reactor made of a material comprising a base layer made of a material M1 and an inner layer made of a material M2, said base layer and said inner layer being laid against each other by bonding.

According to a preferred embodiment, the rate of corrosion of the material M2, measured according to ASTM D 2 328-65 T, is less than 1 mm/year.

According to a preferred embodiment, the bonding is performed by weld bonding, explosive bonding, hot-roll bonding or cold-roll bonding, preferably by explosive bonding or hot-roll bonding.

According to a preferred embodiment, the material M2 is in contact with the hydrocarbon compound and has a tensile strength less than that of the material M1.

According to a preferred embodiment, the material M2 is in contact with the hydrocarbon compound and has an elongation greater than that of the material M1.

According to a preferred embodiment, said inner layer has a thickness of between 0.05 and 10 mm, said thickness of said inner layer being less than that of said base layer.

According to a preferred embodiment, the material M2 comprises at least 40% by weight of nickel on the basis of the total weight of the material M2.

According to a preferred embodiment, the material M1 comprises at least 70% of iron; advantageously, said base layer comprises less than 0.2% of carbon and/or less than 1% of molybdenum and/or less than 2% of chromium on the basis of the total weight of the material M1.

According to a preferred embodiment, said hydrocarbon compound is of formula (I) $CX(Y)_2—CX(Y)_m—CH_mXY$, in which X and Y independently represent H, F or Cl and m=0 or 1 with at least one from among X or Y which is Cl or F.

According to a preferred embodiment, the hydrocarbon compound is chosen from the group consisting of tetrachloropropene, chlorotrifluoropropene, pentachloropropane, dichlorotrifluoropropane, trichlorodifluoropropane, tetrafluorochloropropane, tetrachlorofluoropropane, dichlorodifluoropropene, trichlorofluoropropene, pentafluoropropane and mixtures thereof; preferably, the hydrocarbon compound is chosen from the group consisting of 2-chloro-3,3,3-trifluoro-1-propene (HFCO-1233xf), 2,3-dichloro-1,1,1-trifluoropropane (HCFC-243db), 1,1,1,2,3-pentachloropropane (HCC-240db), 1,1,2,2,3-pentachloropropane (HCC-240aa), 1,1,1,3,3-pentachloropropane (HCC-240fa), 1,1,2,3-tetrachloro-1-propene (HCO-1230xa), 2,3,3,3-tetrachloro-1-propene (HCO-1230xf), 1,1,3,3-tetrachloro-1-propene (HCO-1230za), 1,3,3,3-tetrachloro-1-propene (HCO-1230zd), 1,1,1,2,2-pentafluoropropane (HFC-245cb) and 1-chloro-3,3,3-trifluoro-1-propene (HCFO-1233zd).

According to a preferred embodiment, the fluorine content of the hydrocarbon compound is increased by reacting said hydrocarbon compound with hydrogen fluoride in the gas phase in the presence of said catalytic composition, the hydrocarbon compound being a saturated halogenated hydrocarbon or an unsaturated halogenated hydrocarbon or an unsaturated hydrocarbon.

According to a preferred embodiment, the fluorine content of the hydrocarbon compound is reduced by dehydrofluorination of said hydrocarbon compound in the presence of said catalytic composition, said hydrocarbon compound being a fluorinated hydrocarbon compound.

According to a preferred embodiment, the fluorine distribution of the hydrocarbon compound is modified by isomerizing said hydrocarbon compound in the presence of said catalytic composition, said hydrocarbon compound being a fluorinated hydrocarbon compound.

According to a preferred embodiment, the fluorine distribution of the hydrocarbon compound is modified by dismutating said hydrocarbon compound in the gas phase in the presence of said catalytic composition, said hydrocarbon compound being a chlorofluorinated hydrocarbon compound.

According to a preferred embodiment, the fluorine content of the hydrocarbon compound is reduced by reacting said hydrocarbon compound with hydrogen chloride in the gas phase in the presence of said catalytic composition, said hydrocarbon compound being a halogenated hydrocarbon compound containing at least one fluorine atom.

According to a preferred embodiment, the fluorine content of a first hydrocarbon compound is increased by reacting said first hydrocarbon compound with hydrogen fluoride in the gas phase in the presence of a catalytic composition comprising a chromium-based catalyst, the first hydrocarbon compound being a saturated halogenated hydrocarbon or an unsaturated halogenated hydrocarbon or an unsaturated hydrocarbon, and in which the fluorine content of a second hydrocarbon compound is reduced by dehydrofluorinating said second hydrocarbon compound in the presence of said catalytic composition, said second hydrocarbon compound being a fluorinated hydrocarbon compound.

DETAILED DESCRIPTION OF THE INVENTION

In a first aspect of the present invention, a process for modifying the fluorine distribution in a hydrocarbon compound in the presence of a catalytic composition is provided. In this process, the catalytic composition comprises a chromium-based catalyst. Preferably, the chromium-based catalyst may be a chromium oxide (for example $CrO_3$ or $Cr_2O_3$), a chromium oxyfluoride or a chromium fluoride (for example $CrF_3$) or a mixture thereof. The chromium oxyfluoride may have a fluorine content of between 1% and 60% by weight on the basis of the total weight of the chromium oxyfluoride, advantageously between 5% and 55% by weight, preferably between 10% and 52% by weight, more preferentially between 15% and 52% by weight, in particular between 20% and 50% by weight, more particularly between 25% and 45% by weight, favorably between 30% and 45% by weight, more favorably from 35% to 45% by weight of fluorine on the basis of the total weight of chromium oxyfluoride. The catalytic composition may also comprise a cocatalyst chosen from the group consisting of Ni, Co, Zn, Mg, Mn, Fe, Zn, Ti, V, Zr, Mo, Ge, Sn, Pb, Sb; preferably Ni, Co, Zn, Mg, Mn; in particular Ni, Co, Zn. The weight content of the cocatalyst is between 1% and 10% by weight on the basis of the total weight of the catalytic composition. The catalytic composition may also comprise a support such as alumina, for example in its alpha form, activated alumina, aluminum halides (for example $AlF_3$), aluminum oxyhalides, active charcoal, magnesium fluoride or graphite. Preferably, the catalytic composition has a specific surface area of between 1 and 100 $m^2/g$, preferably between 5 and 80 $m^2/g$, more preferentially between 5 and 70 $m^2/g$, ideally between 5 and 50 $m^2/g$, in particular between 10 and 50 $m^2/g$, more particularly between 15 and 45 $m^2/g$.

The catalysts provided according to the present invention may be used to modify the fluorine distribution in hydrocarbon compounds, the latter being halogenated or non-halogenated hydrocarbon compounds. The fluorine distribution in a hydrocarbon compound can be modified by increasing the fluorine content of the hydrocarbon compound. The fluorine distribution of a hydrocarbon compound can also be modified by reducing the fluorine content of the hydrocarbon compound and/or by rearranging the positions of fluorine atoms on the carbon atoms of the hydrocarbon compound.

The present invention can provide processes in which the fluorine distribution in hydrocarbon compounds containing between one and twelve carbon atoms is modified, preferably processes in which the fluorine distribution in hydrocarbon compounds containing between one and six carbon atoms is modified, in particular processes in which the fluorine distribution in hydrocarbon compounds containing three carbon atoms is modified, more particularly in which the fluorine distribution in halogenated hydrocarbon compounds containing three carbon atoms is modified. The present invention can provide processes in which the fluorine content of hydrocarbon compounds containing between one and twelve carbon atoms is increased, preferably processes in which the fluorine content of hydrocarbon compounds containing between one and six carbon atoms is increased, in particular processes in which the fluorine content of hydrocarbon compounds containing three carbon atoms is increased, more particularly processes in which the fluorine content of halogenated hydrocarbon compounds containing three carbon atoms is increased. The processes for modifying the fluorine distribution of hydrocarbon compounds, preferably of halogenated hydrocarbon compounds, include fluorination, chlorofluorination, isomerization, dismutation, dehydrofluorination and chlorodefluorination.

The hydrocarbon compounds include those of general formula $C_hH_aBr_bCl_cF_d$, in which h is an integer between 1 and 6, a is an integer between 0 and 13, b is an integer between 0 and 4, c is an integer between 0 and 13, d is an integer between 0 and 13, and the sum of a, b, c and d is equal to 2h+2; or those of general formula $C_pH_eBr_fCl_gF_h$, in which p is an integer between 2 and 6, e is an integer between 0 and 10, f is an integer between 0 and 2, g is an integer between 0 and 12, h is an integer between 0 and 11, and the sum of e, f, g and h is equal to 2p. Preferably, the hydrocarbon compounds include those of general formula $C_hH_aCl_cF_d$, in which h is an integer between 2 and 4, a is an integer between 0 and 9, c is an integer between 0 and 9, d is an integer between 0 and 9, and the sum of a, c and d is equal to 2h+2; or those of general formula $C_pH_eCl_gF_h$, in which p is an integer between 2 and 4, e is an integer between 0 and 8, g is an integer between 0 and 8, h is an integer between 0 and 7, and the sum of e, f, g and h is equal to 2p.

In particular, the hydrocarbon compounds that are suitable for use in the processes according to the present invention are of formula (I) CX(Y)$_2$—CX(Y)$_m$—CH$_m$XY, in which X and Y independently represent H, F or Cl and m=0 or 1 with at least one from X or Y being Cl or F. Preferably, the hydrocarbon compounds may be chosen from the group consisting of tetrachloropropene, chlorotrifluoropropene, pentachloropropane, dichlorotrifluoropropane, trichlorodifluoropropane, tetrachlorofluoropropane, dichlorodifluoropropene, trichlorofluoropropene, pentafluoropropane, tetrafluorochloropropane and mixtures thereof.

Preferably, the hydrocarbon compounds may be chosen from the group consisting of 2-chloro-3,3,3-trifluoro-1-propene (HFCO-1233xf), 2,3-dichloro-1,1,1-trifluoropropane (HCFC-243db), 1,1,1,2,3-pentachloropropane (HCC-240db), 1,1,2,2,3-pentachloropropane (HCC-240aa), 1,1,1,3,3-pentachloropropane (HCC-240fa), 1,1,2,3-tetrachloro-1-propene (HCO-1230xa), 2,3,3,3-tetrachloro-1-propene (HCO-1230xf), 1,1,3,3-tetrachloro-1-propene (HCO-1230za), 1,3,3,3-tetrachloro-1-propene (HCO-1230zd), 1,1,1,2,2-pentafluoropropane (HFC-245cb) and 1-chloro-3,3,3-trifluoro-1-propene (HCFO-1233zd).

Said process according to the present invention is performed in a reactor made of a material comprising a base layer made of a material M1 and an inner layer made of a material M2, said base layer and said inner layer being laid against each other by bonding. The reactor may be a reactor with a fixed catalytic bed or a reactor with a fluidized catalytic bed or a multitubular reactor. Preferably, said reactor is a reactor with a fixed catalytic bed.

According to a preferred embodiment, the degree of corrosion of the material M2 is less than 1 mm/year, advantageously less than 0.5 mm/year, preferably less than 0.1 mm/year, more preferentially less than 0.05 mm/year, in particular less than 0.025 mm/year, more particularly less than 10 µm/year, favorably less than 5 µm/year. This degree is measured according to the coupon method ASTM D 2 328-65 T.

According to a preferred embodiment, the bonding is performed by weld bonding, explosive bonding, hot-roll bonding or cold-roll bonding. Preferably, the bonding is performed by explosive bonding or by hot-roll bonding. In particular, the bonding is performed by explosive bonding.

The material M2 is in contact with the hydrocarbon compound. Preferably, the material M2 may have a tensile strength lower than that of the material M1. Preferably, the material M2 may have an elongation greater than that of the material M1. In particular, the material M2 may have a tensile strength lower than that of the material M1 and an elongation greater than that of the material M1.

According to a preferred embodiment, said inner layer has a thickness of between 0.01 and 20 mm, said thickness of said inner layer being less than that of said base layer. Preferably, said inner layer may have a thickness of between 0.05 and 15 mm, preferably between 0.1 and 10 mm and more preferentially between 0.1 and 5 mm.

Advantageously, the material M2 comprises at least 40% by weight of nickel on the basis of the total weight of the material M2. Preferably, the material M2 comprises at least 45% by weight of nickel, more preferentially at least 50% by weight of nickel, in particular at least 55% by weight of nickel, more particularly at least 60% by weight of nickel, favorably at least 65% by weight of nickel, more favorably at least 70% by weight of nickel on the basis of the total weight of the material M2.

The material M2 may also comprise chromium in a content of less than 35% by weight on the basis of the total weight of the material M2, advantageously less than 30% by weight, preferably less than 20% by weight, more preferentially less than 15% by weight, in particular less than 10% by weight, more particularly less than 5% by weight on the basis of the total weight of the material M2.

The material M2 may also comprise molybdenum in a content of less than 35% by weight on the basis of the total weight of the material M2, advantageously less than 30% by weight, preferably less than 20% by weight, more preferentially less than 15% by weight, in particular less than 10% by weight, more particularly less than 5% by weight on the basis of the total weight of the material M2.

Preferably, the material M2 comprises at least 40% by weight of nickel on the basis of the total weight of the material M2, preferably at least 45% by weight of nickel, more preferentially at least 50% by weight of nickel, in particular at least 55% by weight of nickel, more particularly at least 60% by weight of nickel, favorably at least 65% by weight of nickel, more favorably at least 70% by weight of nickel on the basis of the total weight of the material M2; and less than 35% by weight of chromium, advantageously less than 30% by weight, preferably less than 20% by weight, more preferentially less than 15% by weight, in particular less than 10% by weight, more particularly less than 5% by weight of chromium on the basis of the total weight of the material M2; and less than 35% by weight of molybdenum, advantageously less than 30% by weight, preferably less than 20% by weight, more preferentially less than 15% by weight, in particular less than 10% by weight, more particularly less than 5% by weight of molybdenum on the basis of the total weight of the material M2;

The material M2 may also comprise cobalt in a content of less than 10% by weight on the basis of the total weight of the material M2, advantageously less than 8% by weight, preferably less than 6% by weight, more preferentially less than 4% by weight, in particular less than 3% by weight, more particularly less than 2% by weight on the basis of the total weight of the material M2.

The material M2 may also comprise tungsten in a content of less than 10% by weight on the basis of the total weight of the material M2, advantageously less than 9% by weight, preferably less than 8% by weight, more preferentially less than 7% by weight, in particular less than 6% by weight, more particularly less than 5% by weight on the basis of the total weight of the material M2.

The material M2 may also comprise iron in a content of less than 25% by weight on the basis of the total weight of the material M2, advantageously less than 20% by weight, preferably less than 15% by weight, more preferentially less than 10% by weight, in particular less than 7% by weight, more particularly less than 5% by weight on the basis of the total weight of the material M2.

The material M2 may also comprise manganese in a content of less than 5% by weight on the basis of the total weight of the alloy, advantageously less than 4% by weight, preferably less than 3% by weight, more preferentially less than 2% by weight, in particular less than 1% by weight, more particularly less than 0.5% by weight on the basis of the total weight of the material M2.

The material M2 may also comprise copper in a content of less than 50% by weight, advantageously less than 45% by weight, preferably less than 40% by weight, more preferentially less than 35% by weight, in particular less than 30% by weight, more particularly less than 25% by weight of copper on the basis of the total weight of the material M2.

Preferably, the material M2 comprises at least 40% by weight of nickel on the basis of the total weight of the material M2, preferably at least 45% by weight of nickel, more preferentially at least 50% by weight of nickel, in particular at least 55% by weight of nickel, more particularly at least 60% by weight of nickel, favorably at least 65% by weight of nickel, more favorably at least 70% by weight of nickel on the basis of the total weight of the material M2; and less than 50% by weight, advantageously less than 45% by weight, preferably less than 40% by weight, more preferentially less than 35% by weight, in particular less than 30% by weight, more particularly less than 25% by weight of copper on the basis of the total weight of the material M2.

Preferably, the material M2 comprises at least 40% by weight of nickel on the basis of the total weight of the material M2, preferably at least 45% by weight of nickel, more preferentially at least 50% by weight of nickel, in particular at least 55% by weight of nickel, more particularly at least 60% by weight of nickel, favorably at least 65% by weight of nickel, more favorably at least 70% by weight of nickel on the basis of the total weight of the material M2; and less than 35% by weight of chromium, advantageously less than 30% by weight, preferably less than 20% by weight, more preferentially less than 15% by weight, in particular less than 10% by weight, more particularly less than 5% by weight of chromium on the basis of the total weight of the material M2; and less than 35% by weight of molybdenum, advantageously less than 30% by weight, preferably less than 20% by weight, more preferentially less than 15% by weight, in particular less than 10% by weight, more particularly less than 5% by weight of molybdenum on the basis of the total weight of the material M2; and less than 25% by weight of iron, advantageously less than 20% by weight, preferably less than 15% by weight, more preferentially less than 10% by weight, in particular less than 7% by weight, more particularly less than 5% by weight of iron on the basis of the total weight of the material M2.

The material M2 may comprise less than 4% by weight of titanium on the basis of the total weight of the material M2, advantageously less than 3% by weight, preferably less than 2% by weight, more preferentially less than 1% by weight, in particular less than 0.5% by weight of titanium, more particularly less than 0.05% by weight of titanium on the basis of the total weight of the material M2; favorably, the material M2 is free of titanium.

The material M2 may comprise less than 4% by weight of niobium on the basis of the total weight of the material M2, advantageously less than 3% by weight, preferably less than 2% by weight, more preferentially less than 1% by weight, in particular less than 0.5% by weight of titanium, more particularly less than 0.05% by weight of niobium on the basis of the total weight of the material M2; favorably, the material M2 is free of niobium.

According to a preferred embodiment, the material M1 comprises at least 70% by weight of iron, advantageously at least 75% by weight, preferably at least 80% by weight, more preferentially at least 85% by weight, in particular at least 90% by weight, more particularly at least 95% by weight of iron on the basis of the total weight of the material M1.

The material M1 may also comprise less than 2% by weight of carbon, advantageously less than 1.5% by weight, preferably less than 1% by weight, more preferentially less than 0.75% by weight, in particular less than 0.5% by weight, more particularly less than 0.2% by weight, favorably less than 0.1% by weight on the basis of the total weight of the material M1. More particularly, the material M1 may comprise between 0.01% and 0.2% by weight of carbon on the basis of the total weight of the material M1.

The material M1 may also comprise less than 2% by weight of molybdenum, advantageously less than 1.5% by weight, preferably less than 1.25% by weight, more preferentially less than 1% by weight of molybdenum on the basis of the total weight of the material M1. More particularly, the material M1 may comprise between 0.1% and 1% by weight of molybdenum on the basis of the total weight of the material M1.

The material M1 may also comprise less than 5% by weight of chromium, advantageously less than 4% by weight, preferably less than 3% by weight, more preferentially less than 2% by weight, in particular less than 1% by weight of chromium on the basis of the total weight of the material M1. More particularly, the material M1 may comprise between 0.5% and 2% by weight of chromium on the basis of the total weight of the material M1.

The material M1 may also comprise less than 2% by weight of silicon, advantageously less than 1.5% by weight, preferably less than 1.25% by weight, more preferentially less than 1% by weight of silicon on the basis of the total weight of the material M1. More particularly, the material M1 may comprise between 0.1% and 1.5% by weight of silicon on the basis of the total weight of the material M1.

The material M1 may also comprise less than 2% by weight of manganese, advantageously less than 1.5% by weight, preferably less than 1.25% by weight, more preferentially less than 1% by weight of manganese on the basis of the total weight of the material M1. More particularly, the material M1 may comprise between 0.1% and 1% by weight of manganese on the basis of the total weight of the material M1.

Thus, the reactor used in the processes according to the invention comprises a base layer made of a material M1 and an inner layer, in contact with at least the hydrocarbon compound, made of a material M2 laid against each other by bonding; said material M2 comprising:

at least 40% by weight of nickel on the basis of the total weight of the material M2, preferably at least 45% by weight of nickel, more preferentially at least 50% by weight of nickel, in particular at least 55% by weight of nickel, more particularly at least 60% by weight of nickel, favorably at least 65% by weight of nickel, more favorably at least 70% by weight of nickel on the basis of the total weight of the material M2; and less than 35% by weight of chromium, advantageously less than 30% by weight, preferably less than 20% by weight, more preferentially less than 15% by weight, in particular less than 10% by weight, more particularly less than 5% by weight of chromium on the basis of the total weight of the material M2; and less than 35% by weight of molybdenum, advantageously less than 30% by weight, preferably less than 20% by weight, more preferentially less than 15% by weight, in particular less than 10% by weight, more particularly less than 5% by weight of molybdenum on the basis of the total weight of the material M2; and less than 25% by weight of iron, advantageously less than 20% by weight, preferably less than 15% by weight, more preferentially less than 10% by weight, in particular less than 7% by weight, more particularly less than 5% by weight of iron on the basis of the total weight of the material M2; or at least 40% by weight of nickel on the basis of the total weight of the material M2, preferably at least 45% by weight of nickel, more preferentially at least 50% by weight of nickel, in particular at least 55% by weight of nickel, more particularly at least 60% by weight of nickel, favorably at least 65% by weight of nickel, more favorably at least 70% by weight of nickel on the basis of the total weight of the material M2; and less than 50% by weight, advantageously less than 45% by weight, preferably less than 40% by weight, more preferentially less than 35% by weight, in particular less than 30% by weight, more particularly less than 25% by weight of copper on the basis of the total weight of the material M2; or at least 40% by weight of nickel on the basis of the total weight of the material M2, preferably at least 45% by weight of nickel, more preferentially at least 50% by weight of nickel, in particular at least 55% by weight of nickel, more particularly at least 60% by weight of nickel, favorably at least 65% by weight of nickel, more favorably at least 70% by weight of nickel on the basis of the total weight of the material M2; and less than 35% by weight of chromium, advantageously less than 30% by weight, preferably less than 20% by weight, more preferentially less than 15% by weight, in particular less than 10% by weight, more particularly less than 5% by weight of chromium on the basis of the total weight of the material M2; and less than 35% by weight of molybdenum, advantageously less than 30% by weight, preferably less than 20% by weight, more preferentially less than 15% by weight, in particular less than 10% by weight, more particularly less than 5% by weight of molybdenum on the basis of the total weight of the material M2;

and the material M1 comprising:

at least 70% by weight of iron, advantageously at least 75% by weight, preferably at least 80% by weight, more preferentially at least 85% by weight, in particular at least 90% by weight, more particularly at least 95% by weight of iron on the basis of the total weight of the material M1; and less than 2% by weight of carbon, advantageously less than 1.5% by weight, preferably less than 1% by weight, more preferentially less than 0.75% by weight, in particular less than 0.5% by weight, more particularly less than 0.2% by weight, favorably less than 0.1% by weight on the basis of the total weight of the material M1, more particularly between 0.01% and 0.2% by weight of carbon on the basis of the total weight of the material M1 and less than 2% by weight of molybdenum, advantageously less than 1.5% by weight, preferably less than 1.25% by weight, more preferentially less than 1% by weight of molybdenum on the basis of the total weight of the material M1, more particularly between 0.1% and 1% by weight of molybdenum on the basis of the total weight of the material M1; and/or less than 5% by weight of chromium, advantageously less than 4% by weight, preferably less than 3% by weight, more preferentially less than 2% by weight, in particular less than 1% by weight of chromium on the basis of the total weight of the material M1, more particularly between 0.5% and 2% by weight of chromium on the basis of the total weight of the material M1.

Preferably, the reactor is fed with hydrocarbon compound via feed lines. The reactor also comprises effluent or outlet lines for removing the reaction mixture from the reactor.

Preferably, the feed or outlet lines of the reactor are made of a specific material that is also capable of withstanding corrosion, for example made of the material M2. The feed lines may be of tubular shape. Alternatively, the feed or outlet lines may be made of a material comprising a base layer made of a material M1 covered with an inner layer, in contact with the hydrocarbon or another starting material, for example HF, made of a material M2.

The reactor also comprises one or more dephlegmators, one or more dip tubes, one or more devices for introducing the starting materials, and one or more gratings for supporting and retaining the catalyst. Said one or more dephlegmators and/or said one or more dip tubes and/or said one or more devices for introducing the starting materials and/or said one or more gratings for supporting and retaining the catalyst may be made of a material comprising a base layer made of a material M1 covered with an inner layer, in contact with the hydrocarbon or another starting material, for example HF, made of a material M2. The materials M1 and M2 are as described above.

In a first embodiment, the fluorine content of the hydrocarbon compound is increased by reacting said compound with hydrogen fluoride in the presence of said catalytic composition, the hydrocarbon compound being a saturated halogenated hydrocarbon or an unsaturated halogenated hydrocarbon or an unsaturated hydrocarbon. A hydrocarbon compound is halogenated when it comprises at least one halogen. A hydrocarbon is unsaturated when it contains at least one carbon-carbon double bond.

Hydrocarbon compounds that are suitable as starting reagents for the fluorination process of this first embodiment may be saturated or unsaturated halogenated hydrocarbon compounds. The saturated halogenated hydrocarbon compounds include those of general formula $C_hH_aBr_bCl_cF_d$, in which h is an integer between 1 and 6, a is an integer between 0 and 13, b is an integer between 0 and 4, c is an integer between 0 and 13, d is an integer between 0 and 13, and the sum of a, b, c and d is equal to 2h+2, provided that b+c is at least equal to 1. Preferably, the saturated halogenated hydrocarbon compounds include those of general formula $C_hH_aCl_cF_d$, in which h is an integer between 2 and 4, a is an integer between 0 and 9, c is an integer between 1 and 9, d is an integer between 0 and 9, and the sum of a, c and d is equal to 2h+2. The unsaturated halogenated hydrocarbon compounds include those of general formula $C_pH_eBr_fCl_gF_h$, in which p is an integer between 2 and 6, e is an integer between 0 and 11, f is an integer between 0 and 2, g is an integer between 0 and 12, h is an integer between 0 and 11, provided that f+g is at least equal to 1, and the sum of e, f, g and h is equal to 2p. Preferably, the unsaturated halogenated hydrocarbon compounds include those of general formula $C_pH_eCl_gF_h$, in which p is an integer between 2 and 4, e is an integer between 0 and 7, g is an integer between 1 and 8, h is an integer between 0 and 7, and the sum of e, g and h is equal to 2p. The fluorine content of the saturated halogenated hydrocarbon compounds of formula $C_hH_aBr_bCl_cF_d$, of the unsaturated halogenated hydrocarbon compounds of formula $C_pH_eBr_fCl_gF_h$, as defined above, may be increased by reacting said hydrocarbon compounds with HF in the vapor phase in the presence of said catalytic composition.

The process according to the first embodiment may be performed in a reactor according to the present invention comprising a catalytic bed containing said catalytic composition and according to the following operating conditions:

an HF/hydrocarbon compound mole ratio between 1:1 and 150:1, preferably between 2:1 and 125:1, more preferentially between 3:1 and 100:1;

a contact time between 1 and 100 s, preferably between 2 and 75 s, in particular between 3 and 50 s;

a pressure between atmospheric pressure and 20 bara, preferably between 2 and 18 bara, more preferentially between 3 and 15 bara;

a temperature, preferably of the catalytic bed, between 200 and 450° C., preferably between 250 and 400° C., more preferentially between 280° C. and 380° C.

The process may be successfully performed over a time of between 10 and 8000 hours, preferably between 50 and 5000 hours, more preferentially between 70 and 1000 hours.

An oxidant, such as oxygen or chlorine, may be added during the process. The mole ratio of the oxidant to the hydrocarbon compound may be between 0.005 and 2, preferably between 0.01 and 1.5. The oxidant may be pure oxygen, air, or a mixture of oxygen and nitrogen.

The amount of HF reacted with the hydrocarbon compounds has to be at least stoichiometric. The stoichiometric amount is based on the number of Br and/or Cl substituents to be replaced with F, in addition to one mole of HF to saturate the carbon-carbon double bond(s), if any.

Examples of saturated halogenated compounds of formula $C_nH_aBr_bCl_cF_d$ that may be reacted with HF in the presence of the catalysts of this invention include $CH_2Cl_2$, $CH_2Br_2$, $CHCl_3$, $CCl_4$, $C_2Cl_6$, $C_2BrCl_5$, $C_2Cl_5F$, $C_2Cl_4F_2$, $C_2Cl_3F_3$, $C_2Cl_2F_4$, $C_2ClF_5$, $C_2HCl_5$, $C_2HCl_4F$, $C_2HCl_3F_2$, $C_2HCl_2F_3$, $C_2HClF_4$, $C_2HBrF_4$, $C_2H_2Cl_4$, $C_2H_2Cl_3F$, $C_2H_2Cl_2F_2$, $C_2H_2ClF_3$, $C_2H_3Cl_3$, $C_2H_3Cl_2F$, $C_2H_3ClF_2$, $C_2H_4Cl_2$, $C_2H_4ClF$, $C_3Cl_6F_2$, $C_3Cl_5F_3$, $C_3Cl_4F_4$, $C_3Cl_3F_5$, $C_3HCl_7$, $C_3HCl_6F$, $C_3HCl_5F_2$, $C_3HCl_4F_3$, $C_3HCl_3F_4$, $C_3HCl_2F_5$, $C_3Cl_2F_6$, $C_3H_2Cl_6$, $C_3H_2BrCl_5$, $C_3H_2Cl_5F$, $C_3H_2Cl_4F_2$, $C_3H_2Cl_3F_3$, $C_3H_2Cl_2F_4$, $C_3H_2ClF_5$, $C_3H_3Cl_5$, $C_3H_3Cl_4F$, $C_3H_3Cl_3F_2$, $C_3H_3Cl_2F_3$, $C_3H_3ClF_4$, $C_3H_4Cl_4$, $C_4Cl_4F_4$, $C_4Cl_4Cl_6$, $C_4H_6Cl_6$, $C_4H_5Cl_4F_1$ and $C_6H_4Cl_8$.

Specific examples of fluorination reactions of saturated halogenated hydrocarbon compounds that may be successfully performed under the conditions described above using the catalysts of this invention include the conversion of 1,1,2-trichloroethane ($CHCl_2CH_2Cl$ or HCC-140) into 1-chloro-2,2-difluoroethane ($CH_2ClCF_2H$ or HCFC-142), the conversion of 1,1,1,3,3,3-hexachlorodifluoropropane ($CCl_3CF_2CCl_3$ or CFC-212ca) into a mixture of 1,1,3-trichloro-1,2,2,3,3-pentafluoropropane ($CCl_2FCF_2CClF_2$ or CFC-215ca) and 1,3-dichloro-1,1,2,2,3,3-hexafluoropropane ($CClF_2CF_2CClF_2$ or CFC-216ca), the conversion of 1,1,1,3,3,3-hexachloropropane ($CCl_3CH_2CCl_3$ or HCC-230fa) into 1-chloro-1,1,3,3,3-pentafluoropropane ($CF_3CH_2CClF_2$ or HCFC-235fa) and 1,1,1,3,3,3-hexafluoropropane ($CF_3CH_2CF_3$ or HFC-236fa), the conversion of 1,1,1,3,3-pentachloropropane ($CCl_3CH_2CHCl_2$ or HCC-240fa) into a mixture of 1,1,1,3,3-pentafluoropropane ($CHF_2CH_2CF_3$ or HFC-245fa), 1-chloro-3,3,3-trifluoro-1-propene ($CHCl=CHCF_3$ or HCFO-1233zd) and 1,3,3,3-tetrafluoropropene ($CHF=CHCF_3$ or HFO-1234ze), the conversion of 2,2,3-trichloro-1,1,1,3,3-pentafluoropropane ($CF_3CCl_2CClF_2$ or CFC-215aa) into a mixture of 1,1,1,3,3,3-hexachlorodifluoropropane ($CF_3CCl_2CF_3$ or CFC-216ca) and 2-chloro-1,1,1,2,3,3,3-heptafluoropropane ($CF_3CClFCF_3$ or CFC-217ba), the conversion of 1,1,1,3,3,3-hexachlorodifluoropropane ($CF_3CCl_2CF_3$ or CFC-216ca) into 2-chloro-1,1,1,2,3,3,3-heptafluoropropane ($CF_3ClFCF_3$ or CFC-217ba), the conversion of a mixture containing 1,1-dichloro-2,2,3,3,3-pentafluoropropane ($CF_3CF_2CHCl_2$ or HCFC-225ca) and 1,3-dichloro-1,2,2,3,3-pentafluoropropane ($CClF_2CF_2CHClF$ or HCFC-225cb) into a mixture of 1-chloro-1,2,2,3,3,3-hexafluoropropane ($CF_3CF_2CHClF$ or HCFC-226ca) and 1,1,1,2,2,3,3-heptafluoropropane ($CF_3CF_2CHF_2$ or HFC-227ca), the conversion of 1,1,1,2,3-pentachloropropane ($CCl_3CHClCH_2Cl$ or HCC-240db) into 2-chloro-3,3,3-trifluoro-1-propene ($CF_3CCl=CH_2$ or HCFO-1233xf), the conversion of 1,1,2,2,3-pentachloropropane ($CHCl_2CCl_2CH_2Cl$ or HCC-240aa) into 2-chloro-3,3,3-trifluoro-1-propene ($CF_3CCl=CH_2$ or HCFO-1233xf), the conversion of 1,1,1,2,3-pentachloropropane ($CCl_3CHClCH_2Cl$ or HCC-240db) into 2,3,3,3-tetrafluoropropene ($CF_3CF=CH_2$ or HFO-1234yf), the conversion of 1,1,2,2,3-pentachloropropane ($CHCl_2CCl_2CH_2Cl$ or HCC-240aa) into 2,3,3,3-tetrafluoropropene ($CF_3CF=CH_2$ or HFO-1234yf), the conversion of 1,1,1,3,3-pentachloropropane ($CCl_3CH_2CHCl_2$ or HCC-240fa) into 1,3,3,3-tetrafluoropropene ($CF_3CH=CHF$ or HFO-1234ze), in particular the conversion of 1,1,1,2,3-pentachloropropane ($CCl_3CHClCH_2Cl$ or HCC-240db) into 2-chloro-3,3,3-trifluoro-1-propene ($CF_3CCl=CH_2$ or HCFO-1233xf), the conversion of 1,1,2,2,3-pentachloropropane ($CHCl_2CCl_2CH_2Cl$ or HCC-240aa) into 2-chloro-3,3,3-trifluoro-1-propene ($CF_3CCl=CH_2$ or HCFO-1233xf), the conversion of 1,1,1,2,3-pentachloropropane ($CCl_3CHClCH_2Cl$ or HCC-240db) into 2,3,3,3-tetrafluoropropene ($CF_3CF=CH_2$ or HFO-1234yf), the conversion of 1,1,2,2,3-pentachloropropane ($CHCl_2CCl_2CH_2Cl$ or HCC-240aa) into 2,3,3,3-tetrafluoropropene ($CF_3CF=CH_2$ or HFO-1234yf), the conversion of 1,1,1,3,3-pentachloropropane ($CCl_3CH_2CHCl_2$ or HCC-240fa) into 1,3,3,3-tetrafluoropropene ($CF_3CH=CHF$ or HFO-1234ze), the conversion of 1,1,2-trichloroethane ($CHCl_2CH_2Cl$ or HCC-140) into 1-chloro-2,2-difluoroethane ($CH_2ClCF_2H$ or HCFC-142).

Examples of halogenated or non-halogenated unsaturated compounds of formulae $C_pH_eBr_fCl_gF_h$ and $C_iH_j$ which may be reacted with HF in the presence of the catalysts of this invention include $C_2Cl_4$, $C_2BrCl_3$, $C_2Cl_3F$, $C_2Cl_2F_2$, $C_2ClF_3$, $C_2F_4$, $C_2HCl_3$, $C_2HBrCl_2$, $C_2HCl_2F$, $C_2HClF_2$, $C_2HF_3$, $C_2H_2Cl_2$, $C_2H_2ClF$, $C_2H_2F_2$, $C_2H_3Cl$, $C_2H_3F$, $C_2H_4$, $C_3H_6$, $C_3H_6Cl$, $C_3H_4Cl_2$, $C_3H_3Cl_3$, $C_3H_2Cl_4$, $C_3HCl_5$, $C_3H_2ClF_3$, $C_3F_3HCl_2$, $C_3F_2H_2Cl_2$, $C_3F_4H$, $ClC_3Cl_6$, $C_3Cl_5F$, $C_3Cl_4F_2$, $C_3Cl_3F_3$, $C_3Cl_2F_4$, $C_3ClF_5$, $C_3HF_5$, $C_3H_2F_4$, $C_3F_6$, $C_4Cl_6$, $C_4Cl_2F_6$, $C_4ClF_7$, $C_4H_2F_6$ and $C_4HClF_6$.

Specific examples of fluorination reactions of unsaturated halogenated hydrocarbon compounds that may be successfully performed using the catalysts of this invention include the conversion of 1,2-dichloroethylene ($CHCl=CClH$ or HCO-1130) into 1-chloro-2,2-difluoroethane ($CH_2ClCF_2H$ or HCFC-142), the conversion of 1,1,2-trichloro-3,3,3-trifluoro-1-propene ($CCl_2=CClCF_3$ or CFC-1213xa) into a mixture of 2,3-dichloro-1,1,1,3,3-pentafluoropropane ($CF_3CHClCClF_2$ or HCFC-225da), 2-chloro-1,1,1,3,3,3-hexafluoropropane ($CF_3CHClCF_3$ or HCFC-226da) and/or 2-chloro-1,1,1,3,3,3-pentafluoro-1-propene ($CF_3CCl=CF_2$ or CFC-1215xc), the conversion of hexafluoropropene ($CF_3CF=CF_2$ or CFC-1216yc) into 1,1,1,2,3,3,3-heptafluoropropane ($CF_3CHFCF_3$ or HFC-227ea), the conversion of 1,1,3,3,3-pentafluoropropene ($CF_3CH=CF_2$ or HFO-1225zc) into 1,1,1,3,3,3-hexafluoropropane ($CF_3CH_2CF_3$ or HFC-236fa), the conversion of 1,3,3,3-tetrafluoropropene ($CF_3CH=CHF$ or HFO-1234ze) into 1,1,1,3,3-pentafluoropropane ($CF_3CH_2CHF_2$ or HFC-245fa), the conversion of 2-chloro-3,3,3-trifluoro-1-propene ($CF_3CCl=CH_2$ or HCFO-1233xf) into 2,3,3,3-tetrafluoropropene ($CF_3CF=CH_2$ or HFO-1234yf), the conversion of 1,1,2,3-tetrachloro-1-propene ($CCl_2=CClCH_2Cl$ or HCO-1230xa) into 2-chloro-3,3,3-trifluoro-1-propene ($CF_3CCl=CH_2$ or HCFO-1233xf) or 2,3,3,3-tetrafluoropropene ($CF_3CF=CH_2$ or HFO-1234yf), the conversion of 2,3,3,3-tetrachloro-1-propene ($CCl_3CCl=CH_2$ or HCO-1230xf) into 2-chloro-3,3,3-trifluoro-1-propene ($CF_3CCl=CH_2$ or HCFO-1233xf) or into 2,3,3,3-tetrafluoropropene ($CF_3CF=CH_2$ or HFO-1234yf), the conversion of 1-chloro-3,3,3-trifluoro-1-propene ($CF_3CH=CHCl$ or HCFO-1233zd) or 1,1,3,3-tetrachloro-1-propene ($CCl_2=CHCHCl_2$ or HCO-1230za) or 1,3,3,3-tetrachloroprop-1-ene (CCl$_3$CH=CHCl or HCO-1230zd) into 1,3,3,3-tetrafluoropropene (CF$_3$CH=CHF or HFO-1234ze), the conversion of 1,1,3,3-tetrachloro-1-propene (CCl$_2$=CHCHCl$_2$ or HCO-1230za) or 1,3,3,3-tetrachloroprop-1-ene (CCl$_3$CH=CHCl or HCO-1230zd) into 1-chloro-3,3,3-trifluoro-1-propene (CF$_3$CH=CHCl or HCFO-1233zd), in particular the conversion of 2-chloro-3,3,3-trifluoro-1-propene (CF$_3$CCl=CH$_2$ or HCFO-1233xf) into 2,3,3,3-tetrafluoropropene (CF$_3$CF=CH$_2$ or HFO-1234yf), the conversion of 1,1,2,3-tetrachloro-1-propene (CCl$_2$=CClCH$_2$Cl or HCO-1230xa) into 2-chloro-3,3,3-trifluoro-1-propene (CF$_3$CCl=CH$_2$ or HCFO-1233xf) or into 2,3,3,3-tetrafluoropropene (CF$_3$CF=CH$_2$ or HFO-1234yf), the conversion of 2,3,3,3-tetrachloro-1-propene (CCl$_3$Cl=CH$_2$ or HCO-1230xf) into 2-chloro-3,3,3-trifluoro-1-propene (CF$_3$CCl=CH$_2$ or HCFO-1233xf) or into 2,3,3,3-tetrafluoropropene (CF$_3$CF=CH$_2$ or HFO-1234yf), the conversion of 1-chloro-3,3,3-trifluoro-1-propene (CF$_3$CH=CHCl or HCFO-1233zd) or 1,1,3,3-tetrachloro-1-propene (CCl$_2$=CHCHCl$_2$ or HCO-1230za) or 1,3,3,3-tetrachloroprop-1-ene (CCl$_3$CH=CHCl or HCO-1230zd) into 1,3,3,3-tetrafluoropropene (CF$_3$CH=CHF or HFO-1234ze), the conversion of 1,2-dichloroethylene (CHCl=CClH or HCO-1130) into 1-chloro-2,2-difluoroethane (CH$_2$ClCF$_2$H or HCFC-142).

Preferentially, the hydrocarbon compound is chosen from the group consisting of 2-chloro-3,3,3-trifluoro-1-propene (HFCO-1233xf), 1,1,1,2,3-pentachloropropane (HCC-240db), 1,1,2,2,3-pentachloropropane (HCC-240aa), 1,1,2,3-tetrachloro-1-propene (HCO-1230xa), 2,3,3,3-tetrachloro-1-propene (HCO-1230xf), or mixtures thereof, for the production of 2,3,3,3-tetrafluoropropene (HFO-1234yf).

Otherwise, the hydrocarbon compound is chosen from the group consisting of 1-chloro-3,3,3-trifluoro-1-propene (HCFO-1233zd), 1,1,1,3,3-pentachloropropane (HCC-240fa), 1,1,3,3-tetrachloro-1-propene (HCO-1230za), 1,3,3,3-tetrachloro-1-propene (HCO-1230zd), or mixtures thereof, for the production of 1,3,3,3-tetrafluoropropene (HFO-1234ze).

In a second embodiment, the fluorine content of the hydrocarbon compound is reduced by dehydrofluorinating said hydrocarbon compound in the presence of said catalytic composition, said hydrocarbon compound being a fluorinated hydrocarbon compound.

The fluorinated hydrocarbon compounds that are suitable as starting materials in the dehydrofluorination process of this invention are typically saturated. The saturated halogenated hydrocarbon compounds include those of general formula $C_nH_aCl_cF_d$, in which n is an integer between 2 and 6, a is an integer between 1 and 13, c is an integer between 0 and 12, d is an integer between 1 and 13, and the sum of a, c and d is equal to 2n+2. Preferably, the saturated halogenated hydrocarbon compounds include those of general formula $C_nH_aCl_cF_d$, in which n is an integer between 2 and 4, a is an integer between 1 and 9, c is an integer between 0 and 6, d is an integer between 1 and 9, and the sum of a, c and d is equal to 2n+2. The fluorine content of the saturated compounds of formula $C_nH_aF_d$ may be reduced in the presence of said catalytic composition.

The process according to the second embodiment may be performed in a reactor comprising a catalytic bed containing a catalyst and according to the following operating conditions:

an HF/hydrocarbon compound mole ratio between 1:1 and 150:1, preferably between 2:1 and 125:1, more preferentially between 3:1 and 100:1;

a contact time between 1 and 100 s, preferably between 2 and 75 s, in particular between 3 and 50 s;

a pressure between atmospheric pressure and 20 bara, preferably between 2 and 18 bara, more preferentially between 3 and 15 bara;

a temperature, preferably of the catalytic bed, between 200 and 450° C., preferably between 250 and 400° C., more preferentially between 280° C. and 380° C.

The process may be successfully performed over a time of between 10 and 8000 hours, preferably between 50 and 5000 hours, more preferentially between 70 and 1000 hours.

An oxidant, such as oxygen or chlorine, may be added during the process. The mole ratio of the oxidant to the hydrocarbon compound may be between 0.005 and 2, preferably between 0.01 and 1.5. The oxidant may be pure oxygen, air, or a mixture of oxygen and nitrogen.

The product of the dehydrofluorination reaction consists of HF and of the unsaturated fluorinated hydrocarbon compound resulting from the loss of HF by the initial reagent. Specific examples of gas-phase dehydrofluorination reactions which may be performed using the catalysts of this invention include the conversion of 1,1-difluoroethane (CHF$_2$CH$_3$ or HFC-152a) into vinyl chloride (CHF=CH$_2$ or HFO-1141), the conversion of 1,1,1-trifluoroethane (CF$_3$CH$_3$ or HFC-143a) into vinylidene fluoride (CF$_2$=CH$_2$ or HFO-1132a), the conversion of 2-chloro-1,1,1-trifluoroethane (CF$_3$CH$_2$Cl or HCFC-133a) into 2-chloro-1,1-difluoroethylene (CF$_2$=CHCl or HCFC-1122), the conversion of 1,1,1,2-tetrafluoroethane (CF$_3$CH$_2$F or HFC-134a) into trifluoroethylene (CF$_2$=CHF or HFO-1123), the conversion of 1,1,2,2-tetrafluoroethane (CHF$_2$CHF$_2$ or HFC-134) into trifluoroethylene (CF$_2$=CHF or HFO-1123), the conversion of 1,1,1,2-tetrafluoropropane (CH$_3$CHFCF$_3$ or HFC-254eb) into 1,1,1-trifluoropropene (CH$_2$=CHCF$_3$ or HFO-1243zf), the conversion of 1,1,1,3,3-pentafluoropropane (CHF$_2$CH$_2$CF$_3$ or HFC-245fa) into 1,3,3,3-tetrafluoropropene (CHF=CHCF$_3$ or HFO-1234ze), the conversion of 1,1,1,2,3,3-hexafluoropropane (CHF$_2$CHFCF$_3$ or HFC-236ea) into 1,2,3,3,3-pentafluoropropene (CHF=CFCF$_3$ or HFO-1225ye), the conversion of 1,1,1,3,3,3-hexafluoropropane (CF$_3$CH$_2$CF$_3$ or HFC-236fa) into 1,1,3,3,3-pentafluoropropene (CF$_3$CH=CF$_2$ or HFO-1225zc), the conversion of 1,1,1,2,3,3-hexafluoropropane (CF$_3$CF$_2$CFH$_2$ or HFC-236cb) into 1,2,3,3,3-pentafluoropropene (CHF=CFCF$_3$ or HFO-1225ye), the conversion of 1,1,1,2,2-pentafluoropropane (CF$_3$CF$_2$CH$_3$ or HFC-245cb) into 2,3,3,3-tetrafluoropropene (CF$_3$CF=CH$_2$ or HFO-1234yf), and the conversion of 1,1,1,2,3-pentafluoropropane (CF$_3$CHFCH$_2$F or HFC-245eb) into 2,3,3,3-tetrafluoropropene (CF$_3$CF=CH$_2$ or HFO-1234yf).

In particular, the halogenated hydrocarbon compound is 1,1,1,2,2-pentafluoropropane (HFC-245cb) for the production of 2,3,3,3-tetrafluoropropene (HFO-1234yf). Otherwise, the halogenated hydrocarbon compound is 1,1,1,3,3-pentafluoropropane (HFC-245fa) for the production of 1,3,3,3-tetrafluoropropene (HFO-1234ze).

In the processes according to the first and the second embodiment, the reaction of said hydrocarbon compound with hydrogen fluoride may be performed in the presence of oxygen or of chlorine.

In a third embodiment, the fluorine distribution in the hydrocarbon compound is modified by isomerizing said hydrocarbon compound in the presence of said catalytic composition, said hydrocarbon compound being a fluorinated hydrocarbon compound.

In a fourth embodiment, the fluorine distribution in the hydrocarbon compound is modified by dismutating said hydrocarbon compound in the gas phase in the presence of said catalytic composition, said hydrocarbon compound being a chlorofluorinated hydrocarbon compound.

The isomerization and dismutation processes of the third and fourth embodiments are successfully performed in the vapor phase in the presence of said catalytic composition.

The fluorinated hydrocarbon compounds that are suitable as starting materials for the isomerization and dismutation processes may be saturated or unsaturated. The saturated fluorinated hydrocarbon compounds that are suitable for the isomerization and dismutation processes include those of general formula $C_nH_aBr_bCl_cF_d$, in which n is an integer between 2 and 6, a is an integer between 0 and 13, b is an integer between 0 and 4, c is an integer between 0 and 13, d is an integer between 1 and 13, and the sum of a, b, c and d is equal to 2n+2, provided that a+b+c≥1. The unsaturated fluorinated hydrocarbon compounds that are suitable for the isomerization and dismutation processes include those of general formula $C_pH_eBr_fCl_gF_h$, in which p is an integer between 2 and 6, e is an integer between 0 and 11, f is an integer between 0 and 2, g is an integer between 0 and 12, h is an integer between 1 and 11, and the sum of e, f, g and h is equal to 2p, provided that the sum e+f+g≥1.

The fluorine distribution of a fluorinated hydrocarbon compound is modified by rearranging the H, Br, Cl and F substituents in the molecule (typically a thermodynamically preferential arrangement) while keeping the same number of H, Br, Cl and F substituents, respectively. In the present document, this process is known as isomerization.

The fluorine distribution of a fluorinated hydrocarbon compound is modified by exchanging at least one F substituent of the halogenated hydrocarbon starting material with at least one H, Br and/or Cl substituent of another molecule of the halogenated hydrocarbon starting material, so as to give the formation of one or more halogenated hydrocarbon compounds having a reduced fluorine content, with respect to the halogenated hydrocarbon starting material, and one or more halogenated hydrocarbon compounds having an increased fluorine content, with respect to the halogenated hydrocarbon starting material. In the present document, this process is known as dismutation.

The isomerization and dismutation reactions may take place simultaneously.

Whether an isomerization, a dismutation or both an isomerization and a dismutation are performed, it is possible to modify the fluorine distribution of saturated compounds of formula $C_nH_aBr_bCl_cF_d$ and/or of unsaturated compounds of formula $C_pH_eBr_fCl_gF_h$ in the presence of a catalyst as disclosed above.

The isomerization and dismutation processes are typically successfully performed at temperatures between approximately 100° C. and 500° C., preferably between approximately 150° C. and approximately 400° C. The contacting time in the reactor is typically from approximately 1 to approximately 120 s, preferably from approximately 5 to approximately 60 s. The isomerization and dismutation reactions may be successfully performed in the presence of an inert gas, such as helium, argon or nitrogen, although this is not preferred. The isomerization and dismutation reactions may be successfully performed in the presence of HF and HCl.

Preferentially, the isomerization processes may be performed using the present catalyst and include the conversion of 1-chloro-1,1-difluoroethane ($CH_3CF_2Cl$ or HCFC-142b) into 1-chloro-2,2-difluoroethane ($CH_2ClCF_2H$ or HCFC-142), the conversion of 1,3-dichloro-1,2,2,3,3-pentafluoropropane ($CHClFCF_2CF_2Cl$ or HCFC-225cb) into 1,1-dichloro-2,2,3,3,3-pentafluoropropane ($CHCl_2CF_2CF_3$ or HCFC-225ca), the conversion of 2,2-dichloro-1,1,1,3,3-pentafluoropropane ($CHF_2CCl_2CF_3$ or HCFC-225aa) into 1,1-dichloro-2,2,3,3,3-pentafluoropropane ($CHCl_2CF_2CF_3$ or HCFC-225ca), the conversion of 1,1,1,2,3-pentafluoropropane ($CF_3CHFCH_2F$ or HFC-245eb) into 1,1,1,2,2-pentafluoropropane ($CF_3CF_2CH_3$ or HFC-245cb), the conversion of 1,1,1,3,3-pentafluoropropane ($CHF_2CH_2CF_3$ or HFC-245fa) into 1,1,1,2,3-pentafluoropropane ($CF_3CHFCH_2F$ or HFC-245eb), the conversion of 1,3,3,3-tetrafluoropropene ($CHF=CHCF_3$ or HFO-1234ze) into 2,3,3,3-tetrafluoropropene ($CF_3CF=CH_2$ or HFO-1234yf), the conversion of 1,1,3,3-tetrafluoropropene ($CF_2=CHCHF_2$ or HFO-1234zc) into 1,3,3,3-tetrafluoropropene ($CHF=CHCF_3$ or HFO-1234ze), the conversion of 1-chloro-3,3,3-trifluoro-1-propene ($CHCl=CHCF_3$ or HCFO-1233zd) into 2-chloro-3,3,3-trifluoro-1-propene ($CH_2=CClCF_3$ or HCFO-1233xf) and the conversion of the (Z) isomer of the hydrochlorofluoroolefins into the (E) isomer of the hydrochlorofluoroolefins.

In particular, the (Z) isomers of hydrochlorofluoroolefins are the (Z) isomers of the hydrochlorofluoropropenes and hydrochlorofluorobutenes. Specific examples include the conversion of (Z)-1-chloro-3,3,3-trifluoro-1-propene ($CHCl=CHCF_3$ or HCFO-1233zd(Z)) into (E)-1-chloro-3,3,3-trifluoro-1-propene ($CHCl=CHCF_3$ or HCFO-1233zd (E)), the conversion of (Z)-1,3,3,3-tetrafluoropropene ($CHF=CHCF_3$ or HFO-1234ze(Z)) into (E)-1,3,3,3-tetrafluoropropene ($CHF=CHCF_3$ or HFO-1234ze(E)), the conversion of (Z)-1,2,3,3,3-pentafluoropropane ($CHF=CFCF_3$ or HFO-1225ye(Z)) into (E)-1,2,3,3,3-pentafluoropropane ($CHF=CFCF_3$ or HFO-1225ye(E)) and the conversion of (Z)-1,1,1,4,4,4-hexafluoro-2-butene ($CF_3CH=CHCF_3$ or HFO-1336mzz(Z)) into (E)-1,1,1,4,4,4-hexafluoro-2-butene ($CF_3CH=CHCF_3$ or HFO-1336mzz (E)).

Preferentially, the dismutation processes may be performed using the present catalyst and include the conversion of chlorofluoromethane ($CH_2ClF$ or HCFC-31) into difluoromethane ($CH_2F_2$ or HFC-32) and dichloromethane ($CH_2Cl_2$ or HCC-30), the conversion of 1-chloro-1,1-difluoroethane ($CH_3CClF_2$ or HCFC-142b) into 1,1,1-trifluoroethane ($CH_3CF_3$ or HFC-143a) and 1,1-dichloro-1-fluoroethane ($CH_3CCl_2F$ or HCFC-141b), the conversion of 1-chloro-1,2,2,2-tetrafluoroethane ($CF_3CHClF$ or HCFC-124) into pentafluoroethane ($CF_3CHF_2$ or HFC-125) and into 2,2-dichloro-1,1,1-trifluoroethane ($CF_3CHCl_2$ or HCFC-123), the conversion of 1,1,3-trichloro-2,2,3,3-tetrafluoropropane ($CHCl_2CF_2CF_2Cl$ or HCFC-224ca) into 1,1-dichloro-2,2,3,3,3-pentafluoropropane ($CHCl_2CF_2CF_3$ or HCFC-225ca) and 1,1,3,3-tetrachloro-1,2,2-trifluoropropane ($CHCl_2CF_2CCl_2F$ or HCFC-223ca), the conversion of 1,1,1,3-tetrafluoro-3-chloropropane ($CF_3CH_2CHClF$ or HCFC-244fa) into 1,1,1,3,3-pentafluoropropane ($CHF_2CH_2CF_3$ or HFC-245fa) and into 1,1,1-trifluoro-3,3-dichloropropane ($CF_3CH_2CHCl_2$ or HCFC-243fa), the conversion of 1,1,2,3-tetrafluoro-1-chloropropane ($CF_2ClCHFCH_2F$ or HCFC-244ec) into 1,1,1,2,3-pentafluoropropane ($CF_3CHFCH_2F$ or HFC-245eb) and into 1,2,3-trifluoro-1,1-dichloropropane ($CFCl_2CHFCH_2F$ or HCFC-243ed), the conversion of 1,1,2,2-tetrafluoro-1-chloropropane ($CF_2ClCF_2CH_3$ or HCFC-244cc) into 1,1,1,2,2-pentafluoropropane ($CF_3CF_2CH_3$ or HFC-245cb) and 1,2,2-trifluoro-1,1-dichloropropane ($CFCl_2CF_2CH_3$ or HCFC-243cc), the conversion of 3-chloro-2,3,3-trifluoro-1-propene ($CH_2=CFCClF_2$ or HCFO-1233yf) into 2,3,3,3-tetrafluoropropene ($CF_3CF=CH_2$ or HFO-1234yf) and into 3,3-dichloro-2,3-difluoro-1-propene ($CH_2$=CFCFCl$_2$ or HCFO-1232yf) and the conversion of 3-chloro-1,3,3-trifluoro-1-propene (CHF=CHCClF$_2$ or HCFO-1233ze) into 1,3,3,3-tetrafluoropropene (CHF=CHCF$_3$ or HFO-1234ze) and 3,3-dichloro-1,3-difluoro-1-propene (CHF=CHCCl$_2$F or HCFO-1232ze).

In a fifth embodiment, the fluorine content of the hydrocarbon compound is reduced by reacting said hydrocarbon compound with hydrogen chloride in the gas phase in the presence of said catalytic composition, said hydrocarbon compound being a halogenated hydrocarbon compound.

The fluorinated hydrocarbon compounds that are suitable as starting materials for the process of this embodiment may be saturated or unsaturated. The saturated halogenated hydrocarbon compounds that are suitable for the chlorodefluorination processes according to this invention include those of general formula $C_nH_aCl_cF_d$, in which n is an integer between 1 and 6, a is an integer between 0 and 13, c is an integer between 0 and 13, d is an integer between 1 and 13, and the sum of a, c and d is equal to 2n+2. The unsaturated halogenated hydrocarbon compounds that are suitable for the chlorodefluorination processes according to this invention include those of general formula $C_pH_eCl_gF_h$, in which p is an integer between 2 and 6, e is an integer between 0 and 11, g is an integer between 0 and 12, h is an integer between 1 and 11, and the sum of e, g and h is equal to 2p.

The chlorodefluorination reactions are typically performed at temperatures of approximately 250° C. to 450° C., preferably of approximately 300° C. to approximately 400° C. The contacting time in the reactor is typically from approximately 1 to approximately 120 s. Needless to say, contact times of approximately 5 to approximately 60 s are possible. The reactions are ideally performed at atmospheric or greater pressure.

The chlorodefluorinations involving saturated halogenated hydrocarbons are particularly worthy of interest. The mole ratio of HCl to the saturated halogenated hydrocarbon compound typically lies between approximately 1:1 and approximately 100:1, preferably from approximately 3:1 to approximately 50:1, and ideally from approximately 4:1 to approximately 30:1. In general, with a given catalytic composition, the higher the temperature, the longer the contact time, the greater the mole ratio of HCl to the saturated halogenated hydrocarbon compound and the greater the conversion of the compounds having a low fluorine content. The above variables can be balanced with respect to each other in order to maximize the formation of chlorinated products.

The product of the chlorodefluorination reactions typically comprises HCl and unreacted HF, unconverted starting material and saturated halogenated hydrocarbon compounds having a lower fluorine content than the starting material as a result of the substitution of one or more fluorine substituents with chlorine.

The reaction products obtained via the processes described in detail in any one of the first five embodiments may be separated via conventional techniques, such as with combinations including, in a nonlimiting manner, washing, settling or distillation. Some of the products of the various embodiments of this invention can form one or more azeotropes with each other or with HF.

The processes disclosed in the present invention may include, in addition, a step of regeneration of said catalytic composition in the presence of a regeneration stream comprising a stream of air/oxidant. The oxidant may be oxygen, air, a mixture of oxygen and nitrogen, chlorine or a mixture of chlorine and nitrogen. When the regeneration is performed with air or a mixture of oxygen and nitrogen, the proportion of oxygen may range from 5 mol % to 100 mol %, relative to the mixture of oxygen and nitrogen. The regeneration step may be performed in the presence of a regeneration stream containing (a) oxygen or air or an oxygen/nitrogen mixture or chlorine and (b) HF. Advantageously, the regeneration stream will contain at least 1 mol % of oxygen, relative to the total regeneration stream. The proportion of oxygen may range from 2 mol % to 98 mol %, relative to the total amount expressed in moles of oxygen and HF, and from 20 mol % to 100 mol %, relative to the total amount expressed in moles of oxygen and nitrogen. The regeneration step is successfully performed at a temperature of 250 to 500° C., preferably of 300 to 450° C., more preferentially of 350 to 400° C. The regeneration step may be successfully performed with a contact time of 1 to 200 s, preferably of 1 to 150 s, more preferentially of 5 to 100 s, and for a period of time of 1 to 1500 hours, preferably of 2 to 1000 hours, more preferentially of 4 to 500 hours, ideally of 10 to 200 hours and in particular of 15 to 150 hours. The regeneration step may be successfully performed under a pressure ranging from atmospheric pressure to 20 bara. In particular, the regeneration step may be successfully performed at a temperature of 250 to 500° C., with a contact time of 1 to 200 s, for 10 to 200 hours and under a pressure between atmospheric pressure and 20 bara.

The processes disclosed in the present invention may comprise, in addition, the step of activation of said catalytic composition in the presence of an air/oxidant stream. Before use, it is preferable for the catalyst to be subjected to a step of activation with air, oxygen or chlorine and/or HF. For example, the catalyst is preferentially subjected to activation with air or oxygen and HF at a temperature between 100 and 500° C., preferably between 250 and 500° C. and in particular between 300 and 400° C. The duration of activation is preferentially from 1 to 200 hours and in particular from 1 to 50 hours. This activation may be followed by a final step of fluorination activation in the presence of an oxidant, HF and hydrocarbon compounds. The HF/hydrocarbon compound mole ratio ranges from 2 to 40 and the oxidant/hydrocarbon compound mole ratio ranges from 0.04 to 25. The temperature of the final step of fluorination activation may range from 300 to 400° C., preferably for a duration of 6 to 100 hours.

Otherwise, the present invention may also provide a process for modifying the chlorine distribution in a hydrocarbon compound in the presence of said catalytic composition. The chlorine content of the hydrocarbon compound is reduced by dehydrochlorination of said hydrocarbon compound in the presence of said catalytic composition, said hydrocarbon compound being a chlorinated hydrocarbon compound. The chlorinated hydrocarbon compounds that are suitable as starting materials for the dehydrochlorination process are typically saturated. The saturated chlorinated hydrocarbon compounds include those of general formula $C_nH_aCl_d$, in which n is an integer between 2 and 6, a is an integer between 1 and 12, d is an integer between 1 and 13, and the sum of a and d is equal to 2n+2. The process according to this alternative embodiment may be performed in a reactor comprising a catalytic bed containing a catalyst and according to the following operating conditions:

contact time of 1 to 100 s, preferably of 2 to 75 s, in particular of 3 to 50 s;

pressure between atmospheric pressure and 20 bara, preferably from 2 to 18 bara, more preferentially from 3 to 15 bara;

temperature, preferably of the catalytic bed, of 200 to 450° C., preferably of 250 to 400° C., more preferentially of 280 to 380° C.

The process may be performed for a period of time of 10 to 8000 hours, preferably of 50 to 5000 hours, more preferentially of 70 to 1000 hours.

The product of the dehydrochlorination reaction consists of HCl and the unsaturated fluorinated hydrocarbon compound resulting from the loss of HCl by the initial reagent. Specific examples of vapor-phase dehydrochlorination reactions may be performed using said catalytic composition include the conversion of 1-chloro-2,2-difluoroethane ($CH_2ClCF_2H$ or HCFC-142) into 1,1-difluoroethylene ($CH_2=CF_2$ or HFO-1132a), the conversion of 1,1,1,3-tetrafluoro-3-chloropropane ($CF_3CH_2CHClF$ or HCFC-244fa) into 1,3,3,3-tetrafluoropropene ($CHF=CHCF_3$ or HFO-1234ze), the conversion of 1,1,1-trifluoro-3,3-dichloropropane ($CF_3CH_2CHCl_2$ or HCFC-243fa) into 1-chloro-3,3,3-trifluoro-1-propene ($CHCl=CHCF_3$ or HCFO-1233zd), the conversion of 2,3-dichloro-1,1,1-trifluoropropane ($CF_3CHClCH_2Cl$ or HCFC-243db) into 2-chloro-3,3,3-trifluoro-1-propene ($CF_3CCl=CH_2$ or HFCO-1233xf), the conversion of 2-chloro-1,1,1,2-tetrafluoropropane ($CF_3CFClCH_3$ or HCFC-244bb) into 2,3,3,3-tetrafluoropropene ($CF_3CF=CH_2$ or HFO-1234yf) and the conversion of 1,1,1,4,4,4-hexafluoro-2-chlorobutane ($CF_3CHClCH_2CF_3$ or HFC-346mdf) into 1,1,1,4,4,4-hexafluoro-2-butene ($CF_3CH=CHCF_3$ or HFO-1336mzz). The process for modifying the chlorine distribution in a hydrocarbon compound may be successfully performed simultaneously with a process for modifying the fluorine distribution in another hydrocarbon compound, for example by increasing or reducing the fluorine content in said other hydrocarbon compound, as described in detail above with reference to the first and the second embodiment. Consequently, the conversion of 2-chloro-1,1,1,2-tetrafluoropropane ($CF_3CFClCH_3$ or HCFC-244bb) into 2,3,3,3-tetrafluoropropene ($CF_3CF=CH_2$ or HFO-1234yf) may be performed with the present catalytic composition simultaneously with the conversion of 2-chloro-3,3,3-trifluoro-1-propene ($CF_3CCl=CH_2$ or HCFO-1233xf) into 2,3,3,3-tetrafluoropropene ($CF_3CF=CH_2$ or HFO-1234yf).

In a sixth embodiment, the fluorine content of a first hydrocarbon compound is increased by reacting said first hydrocarbon compound with hydrogen fluoride in the gas phase in the presence of said catalytic composition, the first hydrocarbon compound being a saturated halogenated hydrocarbon or an unsaturated halogenated hydrocarbon or an unsaturated hydrocarbon, and the fluorine content of a second hydrocarbon compound is reduced by dehydrofluorinating said second hydrocarbon compound in the presence of said catalytic composition, said second hydrocarbon compound being a fluorinated hydrocarbon compound. The first hydrocarbon compound, which is a saturated halogenated hydrocarbon or an unsaturated halogenated hydrocarbon or an unsaturated hydrocarbon, is defined above with reference to the first embodiment. The second hydrocarbon compound is defined above with reference to the second embodiment. The fluorination of the first hydrocarbon compound and the dehydrofluorination of the second hydrocarbon compound are preferentially performed simultaneously.

The process according to the sixth embodiment may be performed in a reactor comprising a catalytic bed containing a catalyst and according to the following operating conditions:

an HF/hydrocarbon compound mole ratio of 1:1 to 150:1, preferably of 2:1 to 125:1, more preferentially of 3:1 to 100:1;

a contact time of 1 to 100 s, preferably of 2 to 75 s, in particular of 3 to 50 s;

pressure between atmospheric pressure and 20 bara, preferably between 2 and 18 bara, more preferentially between 3 and 15 bara;

a temperature (of the catalytic bed) between 200 and 450° C., preferably between 250 and 400° C., more preferentially between 280° C. and 380° C.

The process may be successfully performed over a time of between 10 and 8000 hours, preferably between 50 and 5000 hours, more preferentially between 70 and 1000 hours.

An oxidant, such as oxygen or chlorine, may be added during the process. The mole ratio of the oxidant to the hydrocarbon compound may be between 0.005 and 2, preferably between 0.01 and 1.5. The oxidant may be pure oxygen, air, or a mixture of oxygen and nitrogen.

The products of the reaction are those described in detail with reference to the first and the second embodiment. In particular, the catalytic composition is useful for the conversion of 1,1,1,2,3-pentachloropropane ($CCl_3CHClCH_2Cl$ or HCC-240db) into 2-chloro-3,3,3-trifluoro-1-propene ($CF_3CCl=CH_2$ or HCFO-1233xf) or the conversion of 1,1,1,2,3-pentachloropropane ($CCl_3CHClCH_2Cl$ or HCC-240db) into 2,3,3,3-tetrafluoropropene ($CF_3CF=CH_2$ or HFO-1234yf) or the conversion of 2-chloro-3,3,3-trifluoro-1-propene ($CF_3CCl=CH_2$ or HCFO-1233xf) into 2,3,3,3-tetrafluoropropene ($CF_3CF=CH_2$ or HFO-1234yf) and the conversion of 1,1,1,2,2-pentafluoropropane ($CF_3CF_2CH_3$ or HFC-245cb) into 2,3,3,3-tetrafluoropropene ($CF_3CF=CH_2$ or HFO-1234yf) or the conversion of 1,1,1,2,3-pentafluoropropane ($CF_3CHFCH_2F$ or HFC-245eb) into 2,3,3,3-tetrafluoropropene ($CF_3CF=CH_2$ or HFO-1234yf). In particular, the catalytic composition is useful for the conversion of 2-chloro-3,3,3-trifluoro-1-propene ($CF_3CCl=CH_2$ or HCFO-1233xf) into 2,3,3,3-tetrafluoropropene ($CF_3CF=CH_2$ or HFO-1234yf) and the conversion of 1,1,1,2,2-pentafluoropropane ($CF_3CF_2CH_3$ or HFC-245cb) into 2,3,3,3-tetrafluoropropene ($CF_3CF=CH_2$ or HFO-1234yf).

The process according to the sixth embodiment may be performed in a reactor comprising a catalytic bed containing a catalyst and according to the following operating conditions:

an HF/hydrocarbon compound mole ratio of 1:1 to 150:1, preferably of 2:1 to 125:1, more preferentially of 3:1 to 100:1;

a contact time of 1 to 100 s, preferably of 2 to 75 s, in particular of 3 to 50 s;

pressure between atmospheric pressure and 20 bara, preferably between 2 and 18 bara, more preferentially between 3 and 15 bara;

a temperature, preferably of the catalytic bed, between 200 and 450° C., preferably between 250 and 400° C., more preferentially between 280° C. and 380° C.

The process may be successfully performed over a time of between 10 and 8000 hours, preferably between 50 and 5000 hours, more preferentially between 70 and 1000 hours.

EXAMPLES

Example 1

A coupon consisting (i) of a layer made of a material M1 comprising more than 95% of iron, less than 1% of carbon, less than 1% of molybdenum and less than 1% of chromium and consisting (ii) of a layer made of a material M2 comprising more than 40% of nickel and less than 25% of molybdenum and less than 25% of chromium is placed in a reactor. The reactor also comprises a fixed catalytic bed comprising a chromium oxyfluoride catalyst. 1,1,1,2,3-Pentachloropropane and hydrofluoric acid are introduced into the reactor. The temperature of the catalytic bed ranges from 350° C. to 400° C. The layer made of the material M1 and the layer made of the material M2 are laid against each other by explosive bonding. After 500 hours, no corrosion is observed on the coupon.

Example 2

Example 1 is repeated using a coupon having the same characteristics as those of Example 1, but in which the layer made of the material M1 and the layer made of the material M2 are laid against each other by hot-roll bonding. The materials M1 and M2 are identical to those of Example 1. After 500 hours, no corrosion is observed on the coupon of Example 2.

Comparative Example 1

Example 1 is repeated using a coupon having the same characteristics as those of Example 1, but in which the layer made of the material M1 and the layer made of the material M2 are laid against each other by welding without bonding. The materials M1 and M2 are identical to those of Example 1. After 500 hours, a color change is observed at the interface between the layer made of the material M1 and the layer made of the material M2. The rate of corrosion of the material M2 is 2.0 mm/year under these conditions.

The invention claimed is:

1. A process for modifying the fluorine distribution in a hydrocarbon compound, comprising a step of making contact between said hydrocarbon compound and a catalytic composition comprising a chromium-based catalyst in a reactor, said reactor made of a material comprising a base layer made of a material M1, wherein M1 comprises at least 70% by weight of iron on the basis of the total weight of the material M1, and an inner layer made of a material M2, wherein M2 comprises at least 40% by weight of nickel on the basis of the total weight of the material M2, said base layer and said inner layer being laid against each other by bonding, wherein the material M2 is in contact with the hydrocarbon compound and has a tensile strength less than that of the material M1, wherein the rate of corrosion of the material M2, measured according to ASTM D 2328-65 T, is less than 1 mm/year.

2. A process for modifying the fluorine distribution in a hydrocarbon compound, comprising a step of making contact between said hydrocarbon compound and a catalytic composition comprising a chromium-based catalyst in a reactor, said reactor made of a material comprising a base layer made of a material M1, wherein M1 comprises at least 70% by weight of iron on the basis of the total weight of the material M1, and an inner layer made of a material M2, wherein M2 comprises at least 40% by weight of nickel on the basis of the total weight of the material M2, said base layer and said inner layer being laid against each other by bonding wherein the material M2 is in contact with the hydrocarbon compound and has an elongation greater than that of the material M1, wherein the rate of corrosion of the material M2, measured according to ASTM D 2328-65 T, is less than 1 mm/year.

3. A process for modifying the fluorine distribution in a hydrocarbon compound, comprising a step of making contact between said hydrocarbon compound and a catalytic composition comprising a chromium-based catalyst in a reactor, said reactor made of a material comprising a base layer made of a material M1, wherein M1 comprises at least 70% by weight of iron on the basis of the total weight of the material M1, and an inner layer made of a material M2, wherein M2 comprises at least 40% by weight of nickel on the basis of the total weight of the material M2, said base layer and said inner layer being laid against each other by bonding wherein said inner layer has a thickness of between 0.05 and 10 mm, said thickness of said inner layer being less than that of said base layer, wherein the rate of corrosion of the material M2, measured according to ASTM D 2328-65 T, is less than 1 mm/year.

4. The process as claimed in claim 1, wherein the bonding is performed by weld bonding, explosive bonding, hot-roll bonding or cold-roll bonding.

5. The process as claimed in claim 1, wherein said hydrocarbon compound is of formula (I) $CX(Y)_2$—$CX(Y)_m$—$CH_mXY$, in which X and Y independently represent H, F or Cl and m=0 or 1 with at least one from among X or Y which is Cl or F.

6. The process as claimed in claim 5, wherein the hydrocarbon compound is selected from the group consisting of tetrachloropropene, chlorotrifluoropropene, pentachloropropane, dichlorotrifluoropropane, trichlorodifluoropropane, tetrafluorochloropropane, tetrachlorofluoropropane, dichlorodifluoropropene, trichlorofluoropropene, pentafluoropropane and mixtures thereof.

7. The process as claimed in claim 1, wherein the fluorine content of the hydrocarbon compound is increased by reacting said hydrocarbon compound with hydrogen fluoride in the gas phase in the presence of said catalytic composition, the hydrocarbon compound being a saturated halogenated hydrocarbon or an unsaturated halogenated hydrocarbon or an unsaturated hydrocarbon.

8. The process as claimed in claim 1, wherein the fluorine content of the hydrocarbon compound is reduced by dehydrofluorination of said hydrocarbon compound in the presence of said catalytic composition, said hydrocarbon compound being a fluorinated hydrocarbon compound.

9. The process as claimed in claim 1, wherein the fluorine distribution of the hydrocarbon compound is modified by isomerizing said hydrocarbon compound in the presence of said catalytic composition, said hydrocarbon compound being a fluorinated hydrocarbon compound.

10. The process as claimed in claim 1, wherein the fluorine distribution of the hydrocarbon compound is modified by dismutating said hydrocarbon compound in the gas phase in the presence of said catalytic composition, said hydrocarbon compound being a chlorofluorinated hydrocarbon compound.

11. The process as claimed in claim 1, wherein the fluorine content of the hydrocarbon compound is reduced by reacting said hydrocarbon compound with hydrogen chloride in the gas phase in the presence of said catalytic composition, said hydrocarbon compound being a halogenated hydrocarbon compound containing at least one fluorine atom.

12. The process as claimed in claim 1, wherein the fluorine content of a first hydrocarbon compound is increased by reacting said first hydrocarbon compound with hydrogen fluoride in the gas phase in the presence of a catalytic composition comprising a chromium-based catalyst, the first hydrocarbon compound being a saturated halogenated hydrocarbon or an unsaturated halogenated hydrocarbon or an unsaturated hydrocarbon, and in that the fluorine content of a second hydrocarbon compound is reduced by dehydrofluorinating said second hydrocarbon compound in the presence of said catalytic composition, said second hydrocarbon compound being a fluorinated hydrocarbon compound.

13. The process of claim 1, wherein said base layer comprises less than 0.2% of carbon and/or less than 1% of molybdenum and/or less than 2% of chromium on the basis of the total weight of the material M1.

14. The process of claim 6, wherein the hydrocarbon compound is selected from the group consisting of 2-chloro-3,3,3-trifluoro-1-propene (HFCO-1233xf), 2,3-dichloro-1,1,1-trifluoropropane (HCFC-243db), 1,1,1,2,3-pentachloropropane (HCC-240db), 1,1,2,2,3-pentachloropropane (HCC-240aa), 1,1,1,3,3-pentachloropropane (HCC-240fa), 1,1,2,3-tetrachloro-1-propene (HCO-1230xa), 2,3,3,3-tetrachloro-1-propene (HCO-1230xf), 1,1,3,3-tetrachloro-1-propene (HCO-1230za), 1,3,3,3-tetrachloro-1-propene (HCO-1230zd), 1,1,1,2,2-pentafluoropropane (HFC-245cb) and 1-chloro-3,3,3-trifluoro-1-propene (HCF0-1233zd).

\* \* \* \* \*